United States Patent [19]

Boebel et al.

[11] Patent Number: 4,881,524

[45] Date of Patent: Nov. 21, 1989

[54] INSTSRUMENT FOR GUIDING A LASER LIGHT TRANSMITTING FIBER

[75] Inventors: Manfred Boebel, Oetisheim; Siegfried Hiltebrandt, Knittlingen, both of Fed. Rep. of Germany

[73] Assignee: Richard Wolf, GmbH, Fed. Rep. of Germany

[21] Appl. No.: 301,834

[22] Filed: Jan. 26, 1989

[30] Foreign Application Priority Data

Jan. 27, 1988 [DE] Fed. Rep. of Germany ....... 3802307

[51] Int. Cl.$^4$ .............................................. A61B 1/06
[52] U.S. Cl. ......................................... 128/6; 128/7; 128/8
[58] Field of Search ................................ 128/4, 6, 7, 8

[56] References Cited

U.S. PATENT DOCUMENTS

| | | | |
|---|---|---|---|
| 1,901,731 | 3/1933 | Buerger | 128/7 |
| 2,532,043 | 11/1950 | Wallace | 128/7 |
| 3,858,577 | 1/1975 | Bass et al. | 128/8 |
| 4,313,431 | 2/1982 | Frank | 128/7 |

FOREIGN PATENT DOCUMENTS 2852653 11/1982 Fed. Rep. of Germany .
2945080 4/1986 Fed. Rep. of Germany .
WO 85/02101 5/1985 PCT Int'l Appl. .

Primary Examiner—William H. Grieb
Attorney, Agent, or Firm—Hill, Van Santen, Steadman & Simpson

[57] ABSTRACT

An instrument for guiding a laser light transmitting fiber in intra-abdominal endoscopic work, comprises a shaft to the distal end of which is pivoted a fiber guide for deflecting the distal end of a fiber emerging from the distal end of the shaft. The shaft contains a fiber guide drive tube through which the fiber extends and which is articulated to the fiber guide by means of a link. A lever is provided for shifting the drive tube axially in the shaft to deflect the fiber guide and thus the distal end of the fiber, and a fiber feed device has a fiber feed member mounted for displacement axially of the shaft for advancing and retracting the fiber.

18 Claims, 1 Drawing Sheet

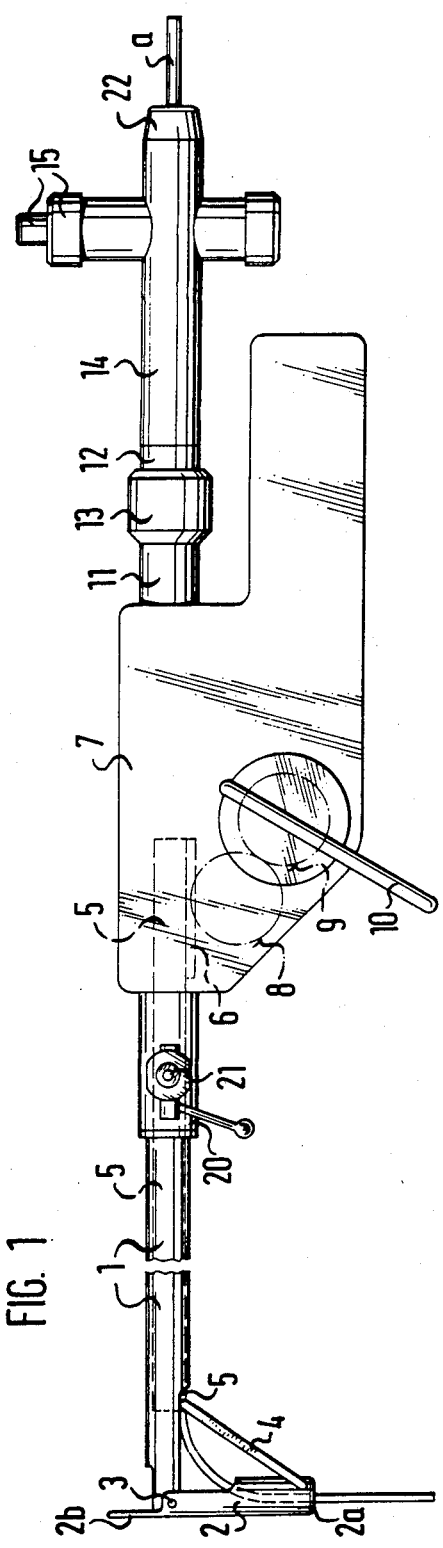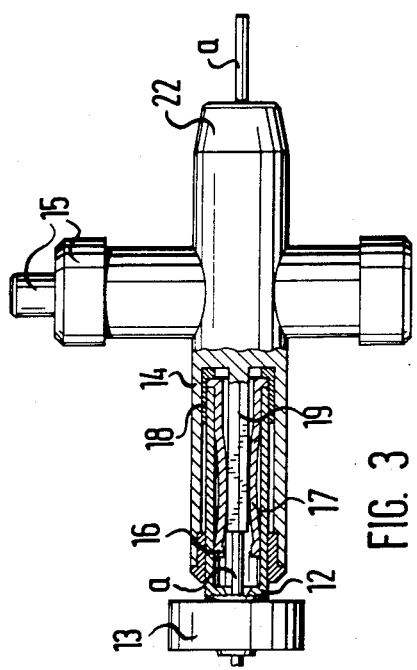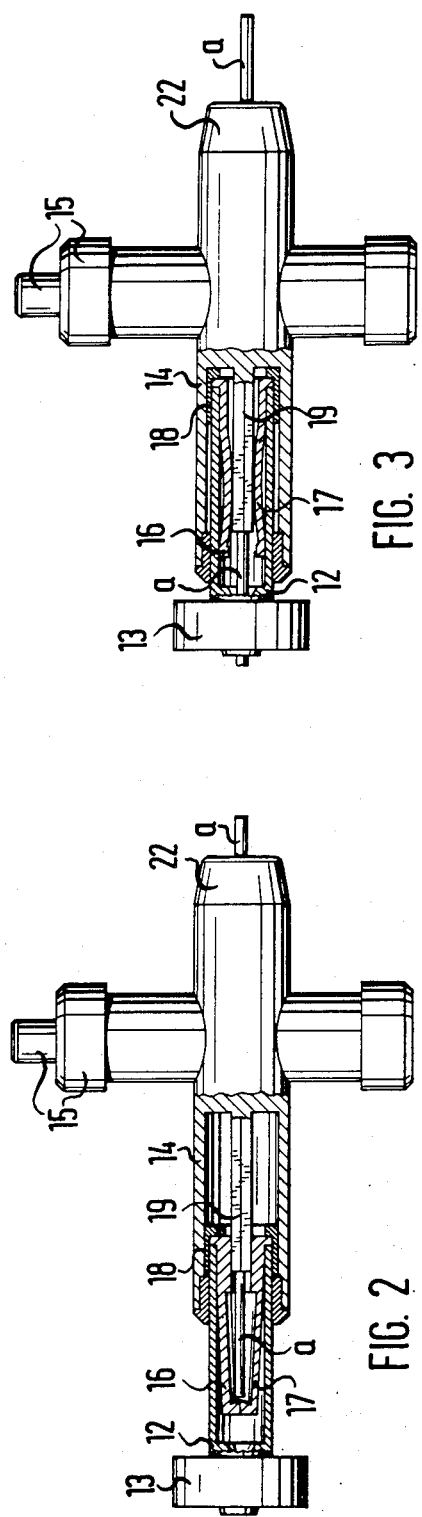

INSTSRUMENT FOR GUIDING A LASER LIGHT TRANSMITTING FIBER

FIELD OF THE INVENTION

This invention relates to an instrument for guiding a laser light transmitting fiber in intra-abdominal endoscopic work.

BACKGROUND OF THE INVENTION

Endoscopic work to be performed intra-abdominally, in particular on the internal genitalia or other parts, is carried out with the use of laser light transmitting fibers, as described, for example, in Federal German Patent Specifications Nos. 28 52 653 and 29 45 080, with the aid of fiber guiding instruments. In such fiber guiding instruments, the fiber is angularly deflected at the distal end of the instrument towards the treatment site, the radius of curvature of such deflection commonly being very small, so that the somewhat brittle fiber is susceptible to breakage. Also, in the known instruments, a fiber deflecting fiber guide pivoted to said distal end is operated by means of a handle which is pivotable about the longitudinal axis of the instrument at the proximal end thereof. Unless the instrument is locally immobilised when the handle is being operated, accidental rotary movement of the distal end of the instrument will occur, whereby the distal end of the fiber is swung out of the treatment site. Further, in the case of these known instruments, the pivotal movement of said fiber guide at the distal end of the instrument and the rotary movement of the handle at the proximal end are contradirectional so that skill and experience in using the instrument are needed if faulty work is to be avoided.

SUMMARY OF THE INVENTION

Objects of the invention are to provide a guiding instrument for the fiber, which is simple and reliable, which facilitates the avoidance of faulty work and with which the distal end of the fiber can be deflected without breaking the fiber. Another object of the invention is to ensure precise setting of the length of the distal end portion of the fiber that projects from the distal end of the instrument, and to ensure that such longitudinal adjustment of the fiber is maintained against accidental displacement, the fiber guide also being usable with the fiber retracted, for free manipulation within the bodily cavity in which the treatment site is.

According to the present invention, in an instrument for guiding a laser light transmitting fiber in intra-abdominal endoscopic work, comprising a shaft to the distal end of which a fiber guide is pivoted, the shaft contains a fiber guide drive tube through which the fiber extends and which is articulated to the fiber guide by means of a link. A lever is provided for shifting the drive tube axially in the shaft to deflect the fiber guide and thus the distal end of the fiber and a fiber feed device is arranged proximally of the drive tube and has a fiber feed member mounted for movement axially of the shaft, for advancing and retracting the fiber.

The radius of deflection of the distal end portion of the fiber can be large enough to avoid risk of its breakage and the instrument is of simple construction and can readily be handled in use.

BRIEF DESCRIPTION OF THE DRAWINGS

FIG. 1 is a side view of a guiding instrument for a laser light transmitting fiber, comprising a lock for the fiber, said system having a distal end and a proximal end.

FIG. 2 is a side view of the proximal end part of the instrument, shown partly in longitudinal section, with the lock in a closed position; and FIG. 3 is a similar view to that of FIG. 2, but showing the lock in an open position.

DETAILED DESCRIPTION OF THE INVENTION

A laser light transmitting fiber guiding instrument, which may be used in conjunction with an endoscope or which may be combined with an endoscope, comprises a shaft 1 having a distal end provided with a deflectable fiber guide 2 pivoted to said distal end by means of a pivot pin 3. The guide 2 comprises a guide sleeve 2a for a laser light transmitting fiber a, in the region of its distal end only, and is joined by way of a link 4 to a fiber guide drive tube 5 extending through the shaft 1. The tube 5 has a toothed rack 6 extending axially thereof and meshing with a gearwheel 8 within a handle in the form of a closed casing 7. The gear wheel 8 meshes with a further gearwheel 9 on a spindle pivotally mounted in the casing 7 and to which is secured a swingable lever 10. In a simpler embodiment, this gearwheel transmission system and the toothed rack may be omitted, the lever 10 in such case being unilaterally mounted above the propelling tube 5 and being pivotally coupled thereto for transmitting motion between the mounting of said lever and the handle casing 7, thereby displacing the tube 5 relative to the casing 7, a detent (not shown) acting against the exterior of the tube 5 to prevent the angular position of the distal end portion of the fiber from being accidentally altered after release of the lever 10. The guide 2 is pivotally displacable from a position of axial alignment with the shaft 1, into the angularly deflected position in which it is shown in FIG. 1, by acting on the lever 10 from its proximal side.

The fiber a can be passed through the tube 5 from its proximal end, to emerge at the distal end of the tube 5, and through the sleeve 2a, so that an unguided length of fiber extends between the tube 5 and the sleeve 2a. The fiber deflecting guide 2 has a rectilinear extension 2b which prevents the fiber from emerging from the distal end of the shaft 1, for example if the guide 2 is, or has been, pivotally deflected from said axially aligned position during the insertion of the fiber through the tube 5.

In the proximal direction, the fiber is led through the handle casing 7 to a fiber feed device which comprises a cylindrical extension 11 of the casing 7, having an inner cylinder in the form of a cylindrical fiber holder 12 connected thereto by means of a coupling 13. An outer cylinder 14 is slidably axially displaceable to a limited extent along the holder 12 and is provided with a clamping device 15 in the form of a trumpet valve, for the fiber passing through it. The outer cylinder 14 is secured against rotation with respect to the holder 12. The holder 12 is provided with an internal lock for the fiber a to be led therethrough, said lock comprising at least two axially prestressed resilient locking arms 16 and 17 which define between them, a cavity which widens in the proximal direction from the closed distal end, the arms 16 and 17 being fixedly joined at their proximal ends to the proximal end of the fiber holder 12, one or more projections of said arms engaging in inner longitudinal grooves 18 in the outer cylinder 14, to prevent rotation of said arms. The outer cylinder 14 is connected at its proximal end through which the fiber is to be threaded, to a tubular plunger 19 through which the fiber can pass freely and which in a fully advanced position of the outer cylinder 14 in the distal direction, pushes the arms 16 and 17 apart to pass the fiber therebetween. In any other axial position of the cylinder 14, the arms 16 and 17 form a lock through which the fiber cannot pass.

In order to prevent twisting of the cylinder 14 with respect to the holder 12 and the instrument as a whole, the passage between the arms 16 and 17 at their proximal end may be non-circular and complementary with the cross-section of the plunger 19, so that the cylinder 14 cannot twist with respect to the holder 12 and the fiber.

A cylinder 20 projecting as an extension from the casing 7 in the distal direction, is provided with a cock 21 for allowing or preventing the passage of a supply of gas or liquid to the distal end of the instrument such fluid being introduced into the tube 5 via longitudinal slots therein to emerge at the distal end thereof. These slots are of smaller width than the diameter of the fiber, so that it cannot seize in the slots.

To prevent gas and liquid losses within the bodily cavity to be examined, the space between the cylinder 20 and the tube 5 is closed at the distal end by means of an O-ring, the fiber feed means 12 to 19 being sealed by means of a cap 22, the interior of the closed casing 7 also being thereby sealed.

In order to use the fiber guiding instrument for endoscopic work, which is to be performed intra-abdominally, the guide 2 is initially pivoted into its position of axial alignment with the shaft 1, the outer cylinder 14 is moved to its distal end position (FIG. 3) and the clamping device 15 is actuated to allow a laser probe fiber to be passed from the proximal end of the instrument, through the sealing cap 22, the tube 5 acting as a guide, and through the guide 2 and its sleeve 2a, until a predetermined length of the fiber projects from the distal end of the instrument. When the instrument is to be inserted into a bodily cavity, that is to say, by way of a trocar sleeve or an instrument passage of an endoscope, the actuation of the clamping device 15 is initially cancelled and the cylinder 14 is moved to its proximal end position (FIG. 2). The fiber centrally traversing the fiber guiding system and being releasably retained by means of the clamping device 15 in the cylinder 14, is thereby retracted in the proximal direction until its distal end is positioned at a predetermined distance behind the distal end of the guide sleeve 2a. In this protected position, the fiber may be inserted into the bodily cavity with the instrument. In order to use the fiber within the bodily cavity, the cylinder 14 is returned to its distal end position (FIG. 3). The length of fiber thereby caused to project from the distal end of the instrument, may then be swung to the required angular position by actuating the lever 10 on the handle casing 7. A detent (not shown) acting directly or indirectly on the lever 10, in the form, for example, of a ball catch or the like, prevents accidental displacement of the guide 2 from said required angular position. After adjustment of the fiber with respect to the site of treatment, the instrument may be used to perform the endoscopic work in hand.

What is claimed is:

1. An instrument for guiding a laser light transmitting fiber in intraabdominal endoscopic work, the instrument comprising a shaft having a distal end and a proximal end and through which said fiber can be passed, a fiber guide deflectably pivoted to said distal end for angularly deflecting an end portion of said fiber projecting from said distal end, and a thrust device for deflecting said fiber guide; said thrust device comprising a fiber guide drive tube extending through said shaft and through which said fiber can be passed to extend up to a proximal end of said fiber guide, a link articulating said fiber guide to said tube, and a lever for displacing said tube axially of said shaft, said instrument further comprising a proximally positioned handle carrying said lever, and a fiber feed device arranged proximally of said tube and having a fiber feed member mounted for limited movement axially of said shaft and being provided with a device for releasably clamping said fiber.

2. An instrument as claimed in claim 1, wherein said feed device comprises an inner cylinder, and an outer cylinder which is slidable to a limited extent along the inner cylinder and is provided with said clamping device through which said fiber can be passed.

3. An instrument as claimed in claim 2, wherein said clamping device is in the form of a trumpet valve.

4. An instrument as claimed in claim 2, wherein said feed device is provided with a lock, said lock comprising a plurality of axially prestressed resilient arms defining a passage for a tubular plunger in said outer cylinder through which plunger said fiber can be passed, the passage and the plunger being of complementary cross-sectional shape so that the outer cylinder cannot twist with respect to the inner cylinder, said plunger serving to spread said arms apart during travel of said outer cylinder along said inner cylinder toward the distal end to allow said fiber to pass between said arms.

5. An instrument as claimed in claim 4, wherein said arms are connected to the inner cylinder at proximal ends thereof by means of outwardly directed projections on said arms, which engage in longitudinal grooves in said outer cylinder.

6. An instrument as claimed in claim 1, wherein said shaft terminates at its proximal end in a cylindrical extension of said handle, said extension being provided with a connector cock, said tube being formed with longitudinal slots for the introduction of fluid thereinto under the control of said cock, each slot being of smaller width than the diameter of said fiber.

7. An instrument as claimed in claim 6, wherein a sealing ring is provided between said tube and said extension, and said handle which is in the form of a closed casing, and said fiber feed device are sealed by means of a sealing cap on said feed device.

8. An instrument as claimed in claim 1, wherein said tube is provided with a toothed rack, said lever being connected to said rack through the agency of at least one gear wheel.

9. An instrument as claimed in claim 1, wherein said lever, which is unilaterally mounted, is pivotally connected to said tube for the transmission of motion between its mounting and said handle.

10. An instrument as claimed in claim 1, comprising a spring loaded detent means for acting on the outer surface of said fiber guide to prevent accidental displacement of said fiber guide and said tube.

11. An instrument as claimed in claim 1, wherein said fiber guide has an extension opposite to a distal end of the fiber guide, for preventing the emergence of said fiber from the distal end of said shaft in a deflected position of the fiber guide, said extension being engageable in a recess in the distal end of said shaft when said fiber guide is axially aligned therewith.

12. An instrument for guiding a laser light transmitting fiber in intra-abdominal endoscopic work, said instrument comprising a shaft having a distal end and a proximal end, a fiber guide deflectably pivoted to the distal end for angular movement relative to the shaft, a fiber guide tube extending through the shaft, a link being connected by an articulating joint to a distal end of the guide tube and having another end of the link being connected to the fiber guide, a lever for displacing said guide tube axially in said shaft to pivot the fiber guide on said distal end of the shaft, a proximally positioned handle carrying said lever, a fiber feed device being arranged proximally of said tube and having a fiber feed member mounted for limited movement axially of said shaft and being provided with a device for releasably clamping said fiber so that a fiber passing through said guide tube has an end portion deflected by said fiber guide angularly to the axis of the shaft.

13. An instrument according to claim 12, wherein said feed device comprising an inner sleeve and an outer sleeve which is slided to a limited extent along the inner sleeve, said outer sleeve being provided with said clamping device, said feed device including a lock comprising a plurality of annular prestressed resilient arms disposed in the inner sleeve, and defining a passage, said outer sleeve having a tubular plunger through which the fiber can pass, said plunger and passage having complementary cross sectional shapes so that the outer sleeve cannot twist with respect to the inner sleeve, said plunger serving to spread said arms apart during travel of the outer sleeve along said inner sleeve towards said distal end of said shaft to allow said fiber to pass between said arms.

14. An instrument according to claim 13, wherein the outer sleeve has longitudinally extending grooves, said arms being connected to the inner sleeve at the proximal end thereof by means of outwardly directed projections on said arms, said projections being engaged in said longitudinal grooves of the outer sleeve.

15. An instrument according to claim 13, wherein said shaft terminates in the proximal end and cylindrical extension of said handle, said handle having a connector cock, said guide tube being formed with longitudinal slots for passing a fluid introduced through said cock into the interior of said guide tube, each of said slots having a width smaller than the diameter of said fiber.

16. An instrument according to claim 15, wherein said handle is formed as a closed casing, a sealing ring is provided between said guide tube and said extension, and said feed device is provided by sealing means in a cap secured thereto.

17. An instrument according to claim 12, wherein the guide tube is provided with a tooth rack, said lever being connected to said rack through at least one gear wheel.

18. An instrument according to claim 12, wherein the fiber guide has an extension opposite to a distal end, said extension preventing the emergence of the fiber from the distal end of said shaft when said fiber guide is in a deflected position.

* * * * *